(12) United States Patent
Hsu et al.

(10) Patent No.: US 10,682,239 B2
(45) Date of Patent: Jun. 16, 2020

(54) EXPANDABLE SPINAL INTERBODY CAGE

(71) Applicant: KE LING BIOTECH LIMITED, Taichung (TW)

(72) Inventors: Shao-Keh Hsu, Taichung (TW); Chien-Yu Lin, New Taipei (TW); Kuo-Wei Tseng, New Taipei (TW)

(73) Assignee: Ke Ling Biotech Limited, Taichung (TW)

( * ) Notice: Subject to any disclaimer, the term of this patent is extended or adjusted under 35 U.S.C. 154(b) by 174 days.

(21) Appl. No.: 15/864,208

(22) Filed: Jan. 8, 2018

(65) Prior Publication Data
US 2018/0193160 A1 Jul. 12, 2018

(30) Foreign Application Priority Data

Jan. 6, 2017 (TW) .............................. 106100530 A
Jul. 7, 2017 (TW) .............................. 106122785 A (51) Int. Cl.
*A61F 2/44* (2006.01)

(52) U.S. Cl.
CPC .............. *A61F 2/447* (2013.01); *A61F 2/4455* (2013.01)

(58) Field of Classification Search
CPC .......... A61F 2/44; A61F 2/4455; A61F 2/446; A61F 2/4465; A61F 2/447; A61F 2002/4475
See application file for complete search history.

(56) References Cited

U.S. PATENT DOCUMENTS

| 8,105,382 | B2 * | 1/2012 | Olmos | A61F 2/4657 |
| | | | | 623/17.15 |
| 8,187,332 | B2 * | 5/2012 | McLuen | A61F 2/4455 |
| | | | | 623/17.16 |
| 8,366,777 | B2 * | 2/2013 | Matthis | A61F 2/4425 |
| | | | | 623/17.16 |

(Continued)

FOREIGN PATENT DOCUMENTS

EP 1925272 A1 5/2008

OTHER PUBLICATIONS

European Extended Search Report and Search Opinion Received for EP Application No. 18150621.3, dated May 15, 2018, 9 pages.

*Primary Examiner* — Eric S Gibson
(74) *Attorney, Agent, or Firm* — TraskBritt (57) ABSTRACT

Disclosed herein is a spinal interbody cage, comprising an upper plate, a lower plate, a screw arbor and two slide blocks. The screw arbor includes a first section with an outer thread and a second section with an outer thread. The outer threads of the first and second sections have opposite directions. The upper plate respectively has a pair of upper plate slanted surfaces proximate to the first and second sections of the screw rod. The lower plate respectively has a pair of lower plate slanted surfaces proximate to the first and second sections. The screw rod is disposed in and cooperates with the inner threads of the slide blocks. The screw rod and slide blocks are arranged between the upper and lower plates. The slide blocks respectively have two slide block slanted surfaces, each abutting and cooperating with one of the upper and lower plate slanted surfaces so as to distance the upper plate from the lower plate when the slide blocks are distanced from each other by rotating the screw rod in one direction.

23 Claims, 6 Drawing Sheets

(56) References Cited

U.S. PATENT DOCUMENTS

| | | | |
|---|---|---|---|
| 8,491,659 B2* | 7/2013 | Weiman | A61F 2/44 623/17.11 |
| 8,518,120 B2* | 8/2013 | Glerum | A61F 2/447 606/279 |
| 8,535,380 B2* | 9/2013 | Greenhalgh | A61B 17/8858 606/90 |
| 8,597,360 B2* | 12/2013 | McLuen | A61F 2/4455 623/17.16 |
| 8,845,734 B2* | 9/2014 | Weiman | A61F 2/442 623/17.16 |
| 8,852,279 B2* | 10/2014 | Weiman | A61F 2/442 623/17.11 |
| 8,894,712 B2* | 11/2014 | Varela | A61F 2/447 623/17.16 |
| 9,233,007 B2* | 1/2016 | Sungarian | A61F 2/442 |
| 9,320,610 B2* | 4/2016 | Alheidt | A61F 2/4611 |
| 9,358,123 B2* | 6/2016 | McLuen | A61F 2/4455 |
| 9,370,434 B2* | 6/2016 | Weiman | A61F 2/44 |
| 9,421,110 B2* | 8/2016 | Masson | A61F 2/446 |
| 9,492,288 B2* | 11/2016 | Wagner | A61F 2/447 |
| 9,801,733 B2* | 10/2017 | Wolters | A61F 2/447 |
| 9,962,270 B2* | 5/2018 | Alheidt | A61F 2/4611 |
| 10,034,769 B2* | 7/2018 | Baynham | A61F 2/447 |
| 10,098,757 B2* | 10/2018 | Logan | A61F 2/447 |
| 10,195,053 B2* | 2/2019 | Kleiner | A61F 2/4455 |
| 10,278,830 B1* | 5/2019 | Walker | A61F 2/442 |
| 10,292,830 B2* | 5/2019 | McLuen | A61F 2/4455 |
| 10,322,007 B2* | 6/2019 | Masson | A61F 2/446 |
| 10,413,422 B2* | 9/2019 | Flower | A61L 27/32 |
| 2008/0140207 A1* | 6/2008 | Olmos | A61F 2/4611 623/17.16 |
| 2010/0211176 A1* | 8/2010 | Greenhalgh | A61F 2/447 623/17.15 |
| 2012/0035729 A1* | 2/2012 | Glerum | A61F 2/447 623/17.15 |
| 2013/0158669 A1* | 6/2013 | Sungarian | A61F 2/442 623/17.16 |
| 2013/0204371 A1* | 8/2013 | McLuen | A61F 2/4455 623/17.16 |
| 2013/0211526 A1* | 8/2013 | Alheidt | A61F 2/4611 623/17.16 |
| 2014/0236296 A1* | 8/2014 | Wagner | A61F 2/447 623/17.15 |
| 2014/0257484 A1* | 9/2014 | Flower | A61F 2/447 623/17.15 |
| 2014/0277500 A1* | 9/2014 | Logan | A61F 2/447 623/17.16 |
| 2014/0336764 A1* | 11/2014 | Masson | A61F 2/446 623/17.15 |
| 2015/0374507 A1* | 12/2015 | Wolters | A61F 2/447 623/17.15 |
| 2016/0081814 A1* | 3/2016 | Baynham | A61F 2/447 623/17.16 |
| 2016/0242932 A1 | 8/2016 | McLuen et al. | |
| 2016/0324651 A1* | 11/2016 | Masson | A61F 2/446 |
| 2018/0193160 A1* | 7/2018 | Hsu | A61F 2/4455 |
| 2019/0231553 A1* | 8/2019 | McLuen | A61F 2/442 |
| 2019/0262139 A1* | 8/2019 | Wolters | A61F 2/4455 |
| 2019/0290446 A1* | 9/2019 | Masson | A61B 17/863 |

* cited by examiner

EXPANDABLE SPINAL INTERBODY CAGE

CROSS-REFERENCE TO RELATED APPLICATION

This application claims the benefit of the filing date of Republic of China Patent Application No. 106100530, filed Jan. 6, 2017, this application also claims the benefit of the filing date of Republic of China Patent Application No. 106122785, filed Jul. 7, 2017, the disclosure of each of which is hereby incorporated herein in its entirety by this reference.

TECHNICAL FIELD

The present invention relates to an interbody cage. Specifically, the present invention relates to an expandable interbody cage.

BACKGROUND

The human spine is composed of several vertebrae and an intervertebral disk. The intervertebral disk is a tissue containing a large amount of water and can absorb the vertical pressure of the spine and provide cushioning effect between upper and lower vertebrae. When any sections of the intervertebral disk change pathologically or due to aging, pain will occur due to compression of the adjacent spinal nerve, resulting in impaired movement.

Regarding the aforementioned problems resulting from injury of the intervertebral disk, conventional techniques offer an approach of implanting an artificial spinal interbody cage. However, the height of the conventional spinal interbody cage is fixed and thus constrains any attempt to minimize wound size.

Figure 6:
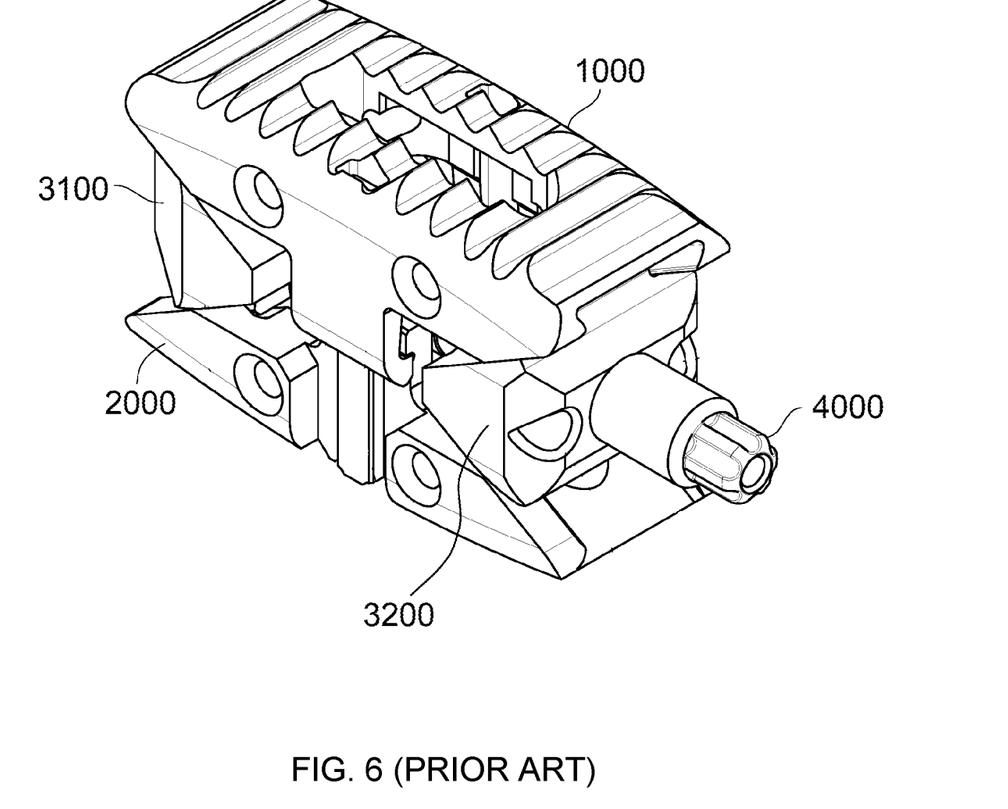
FIG. 6 illustrates a conventional spinal interbody cage.

FIG. 6 shows an adjustable spinal interbody cage employing conventional technique, which is disclosed in the publication (No. 2008/0140207) of a US patent. The conventional spinal interbody cage comprises an actuation shaft 4000, an upper plate 1000, a lower plate 2000 and two wedge members 3100 and 3200. The wedge members 3100 and 3200 upwardly approach each other and contact the upper plate 1000 and the lower plate 2000 in the direction of the axis of the actuation shaft 4000 to force the upper plate to part from the lower plate so as to adjust the height of the spinal interbody cage. However, when the height of the conventional spinal interbody cage is being adjusted, one end of the actuation shaft 4000 will protrude from the longitudinal ends of the upper plate 1000 and the lower plate 2000; such structure will increase the volume of the object implanted between the sections of the vertebra. When the spinal interbody cage is disposed between the sections of the vertebrae with the height adjusted as shown in FIG. 5, the protruding end of the actuation shaft is likely to cause compression to the neighboring nerves or tissues of the sections of the vertebrae, and can also complicate the surgery necessary to implant the spinal interbody cage.

BRIEF SUMMARY

In view of the problems of the conventional spinal interbody cage, it is necessary to provide the industry with a modified expandable spinal interbody cage to minimize the volume of the spinal interbody cage and facilitate height adjustment and implantation surgery.

One embodiment of the subject invention provides an expandable spinal interbody cage, which comprises an opposite first end and a second end in the direction of the long axis, a central area between the first end and the second end, a first side and a second side opposite each other in the lateral direction, a height in the direction perpendicular to the long axis as well as to the lateral direction, an upper plate having a first upper plate surface and a second upper plate surface; a lower plate having a first plate surface distant from the upper plate and a second lower plate surface adjacent to the upper plate, wherein the first upper plate surface is distant from the lower plate relative to the second upper plate surface; a screw arbor disposed between the upper plate and the lower plate and having a first section and a second section, those sections have an outer thread respectively, wherein the outer thread of the first section and the outer thread of the second section are of opposite spiral direction; and a first slide block and a second slide block, wherein the first and the second block are disposed between the upper plate and the lower plate and respectively have a through hole with inner thread, and the inner threads are of opposite spiral direction; wherein the upper plate has a pair of first upper plate slanted surfaces and a pair of second upper plate slanted surfaces adjacent to the first section and the second section of the screw arbor respectively; the upper plate slanted surfaces extend from the second upper plate surface to the first upper plate surface in the direction in which the first end and the second end face the central area; the lower plate has a pair of first lower plate slanted surfaces and a pair of second lower plate slanted surfaces adjacent to the first section and the second section adjacent of the screw arbor respectively; the lower plate slanted surfaces extend from the second lower plate surface to the first lower plate surface in the direction in which the first end and the second end face the central area; the outer thread of the first section of the screw arbor is disposed in the inner thread of the first slide block and the outer thread of the second section of the screw arbor is disposed in the inner thread of the second slide block; and the slide blocks have two pairs of slide block slanted surfaces respectively, wherein the slide block slanted surfaces of the first slide block are adjacent to and abut against the pair of first upper plate slanted surfaces and the pair of first lower plate slanted surfaces, the slide block slanted surfaces of the second slide block are adjacent to and abut against the pair of second upper plate slanted surfaces and the pair of second lower plate slanted surfaces, such that the first slide block distances from the second slide block and the height of the spinal interbody cage increases when the screw arbor is rotated in one direction.

In one embodiment of the subject invention, the pair of first upper plate slanted surfaces is parallel to the pair of second lower plate slanted surfaces and the pair of second upper plate slanted surfaces is parallel and adjacent to the pair of first lower plate slanted surfaces, wherein the pair of first upper plate slanted surfaces and the pair of second upper plate slanted surfaces are symmetric to each other with respect to a surface perpendicular to an axis of the screw arbor, the pair of first lower plate slanted surfaces and the pair of second lower plate slanted surfaces are symmetric to each other with respect to the surface perpendicular to the axis of the screw arbor.

In one embodiment of the subject invention, the upper plate of the spinal interbody cage has an upper plate protruding portion protruding toward the lower plate on the first side and the second side respectively, the upper plate protruding portions have an upper plate constraint member respectively, the lower plate has a lower plate protruding portion on the first side and the second side respectively, wherein the slide blocks, the upper plate and the lower plate are configured so that the slide blocks do not move beyond the upper plate or the lower plate in the direction of the long axis when they are moving on the screw arbor.

In another embodiment of the subject invention, the upper plate has at least one upper plate guide member, the at least one upper plate guide member is correspondingly disposed adjacent to one of the upper plate slanted surfaces, the at least one upper plate guide plate is parallel to the corresponding upper plate slanted surfaces; the lower plate has at least one lower plate guide member, the at least one lower plate guide member is correspondingly disposed adjacent to one of the lower plate slanted surfaces, the at least one lower plate guide plate is parallel to the corresponding lower plate slanted surfaces; and the slide blocks comprise at least two slide block guide members respectively, the slide block guide members mate with the upper plate guide member and the lower plate guide member, wherein the slide block guide members are correspondingly disposed adjacent to one of the slide block slanted surfaces, the slide block guide members mate with the upper plate guide member and the lower plate guide member so as to guide the relative movement of the slide block with the upper plate and the lower plate. In one embodiment of the subject invention, the slide block guide members are protruding rails and the upper plate guide member and the lower plate guide member are grooves, or the slide block guide members are grooves and the upper plate guide member and the lower plate guide member are protruding rails.

In one embodiment of the subject invention, the length of the screw arbor is smaller or equal to the lengths of the upper plate and the lower plate in the direction of the long axis; that is, the screw arbor is disposed between the upper plate and the lower plate and its length in the direction of the long axis will not exceed the upper plate or the lower plate.

In one embodiment of the subject invention, the second upper plate surfaces have an upper plate curved groove on the first end and the second end respectively, and the second lower plate surfaces have a lower plate curved groove on the first end and the second end respectively, wherein when the screw arbor is rotating in the other direction such that the first slide block approaches the second slide block and the height of the spinal interbody cage decreases, the upper plate curved grooves and the lower plate curved grooves serve to accommodate the screw arbor. Further, when the height of the spinal interbody cage is collapsed to the minimum, the respective upper plate curved grooves and the lower plate curved grooves form a circular aperture which surrounds the screw arbor.

In one embodiment of the subject invention, one or each of the upper plate and the lower plate has a curved surface, which is configured to extend, individually or separately, from the first upper plate surface or the first lower plate surface to the direction of the first end on the location adjacent to the central area, such that the thicknesses of the upper plate and the lower plate adjacent to the first end decrease gradually.

In one embodiment of the subject invention, one of the upper plate slanted surfaces of the pair of first upper plate slanted surfaces and one of the upper plate slanted surfaces of the pair of second upper plate slanted surfaces are located on the first side, and the other upper plate slanted surface of the pair of first upper plate slanted surfaces and the other upper plate slanted surface of the pair of second upper plate slanted surfaces are located on the second side; and one of the lower plate slanted surfaces of the pair of first lower plate slanted surfaces and one of the lower plate slanted surfaces of the second lower plate slanted surfaces are located on the first side, and the other lower plate slanted surface of the pair of second lower plate slanted surfaces and the other lower plate slanted surface of the pair of second lower plate slanted surfaces are located on the second side.

In one embodiment of the subject invention, an angle is formed between the first upper plate surface and the first lower plate surface so as to set the angle of the surface desired to be supported between the first plate surface and the second plate surface.

In one embodiment of the subject invention, the angle formed between the first plate surface and the second surface ranges from 0 to 25 degrees or 0 to 12 degrees.

Another embodiment of the subject invention provides an expandable spinal interbody cage, comprising: an upper plate having a serrate structure with a plurality of the upper plate slanted surfaces; a lower plate having a serrate structure with plurality of the lower plate slanted surfaces; a screw arbor disposed between the upper plate and the lower plate and having a first section and a second section, the sections having an outer thread respectively, wherein the outer thread of the first section and the outer thread of the second section are of opposite spiral direction; and a first slide block and a second slide block, wherein the slide blocks are disposed between the upper plate and the lower plate and have a through aperture with inner thread respectively, and the inner threads are of opposite spiral direction, wherein the outer threads of the screw arbor are disposed in and mate with the inner threads of the first slide block and the second slide block, and the screw arbor, the first slide block and the second slide block are disposed between the upper plate and the lower plate; and the respective upper plate slanted surfaces face the lower plate, the respective lower plate slanted surfaces face the upper plate, the first slide blocks and the second slide blocks respectively include at least two slide block slanted surfaces, the slide block slanted surfaces abut against one of the upper plate slanted surfaces and the lower plate slanted surfaces, wherein the upper plate slanted surfaces, the lower plate slanted surfaces and the slide block slanted surfaces are configured so that when the screw arbor is rotating in the direction of the longer axis, the first slide block and the second slide block are driven to distance themselves from each other and causes the upper plate to distance itself from the lower plate in the vertical direction.

In one embodiment of the subject invention, the spinal interbody cage has a first cross-section area on the first end along the direction of the longer axis, and a second cross-section area on the second end along the direction of the longer axis, wherein the first cross-section area is smaller than the second cross-section area. In one embodiment of the subject invention, the spinal interbody cage includes a first upper plate surface and a first lower plate surface, wherein the first upper plate surface is located at one end of the vertical direction, a first lower plate surface is located at the other end of the vertical direction, the first upper plate surface and the first lower plate surface form an angle in between so as to set the angle of the surface desired to be supported between the first plate surface and the second plate surface.

By means of the spinal interbody cage of the subject invention, the height of the spinal interbody cage can be increased or decreased continuously, smoothly and steadily by rotating the screw arbor so as to match the height between the spines of a patient, providing more stable support. Moreover, during the process of adjusting the height of the spinal interbody cage, the screw arbor and the slide block will not exceed the upper plate or the lower plate in the direction of the longitudinal axis, so the risk of the compression of the neighboring spinal nerves and tissues as a result of the structure having a screw arbor exceeding the upper plate and the lower plate in the direction of the long axis can be avoided. And by providing a smaller front end area on the curved surfaces of the first end of the upper and lower plate to guide the implantation of the spinal interbody cage as suggested in the subject invention, the process of surgery will become easier.

BRIEF DESCRIPTION OF THE DRAWINGS

The descriptions of the figures below are solely for exemplification and do not impose any limitations on the scope of the subject invention.

DETAILED DESCRIPTION

Following are the detailed descriptions of the embodiments of the subject invention with reference to the drawings. It should be noted that the content of the embodiments only serves to show the practical configuration of the subject invention and does not impose any limitation on the scope of the claimed invention.

Figure 1:
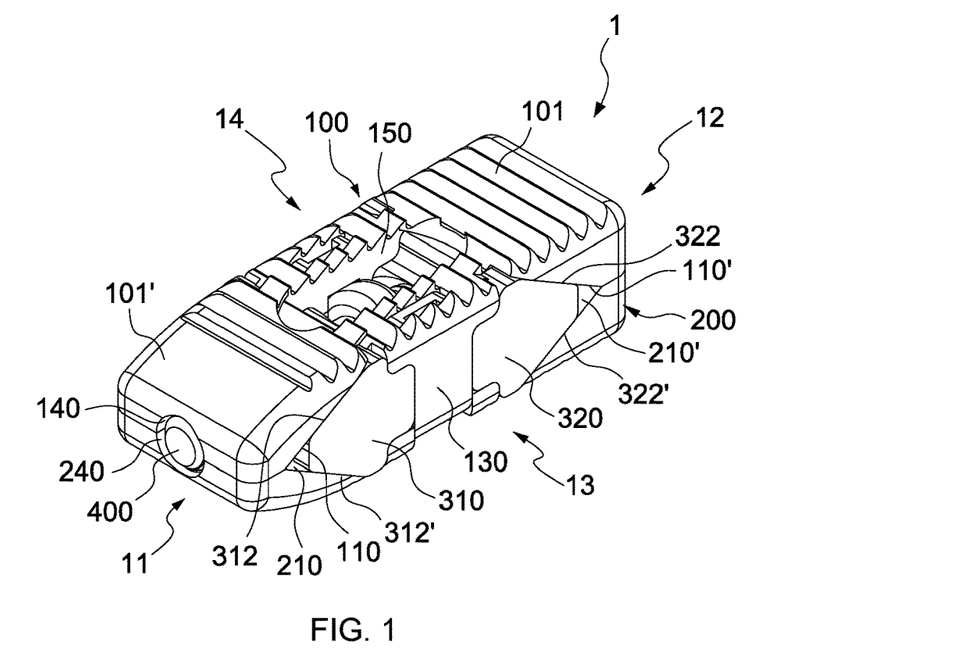
FIG. 1 illustrates the perspective view of the spinal interbody cage of one embodiment of the subject invention.
Figure 2:
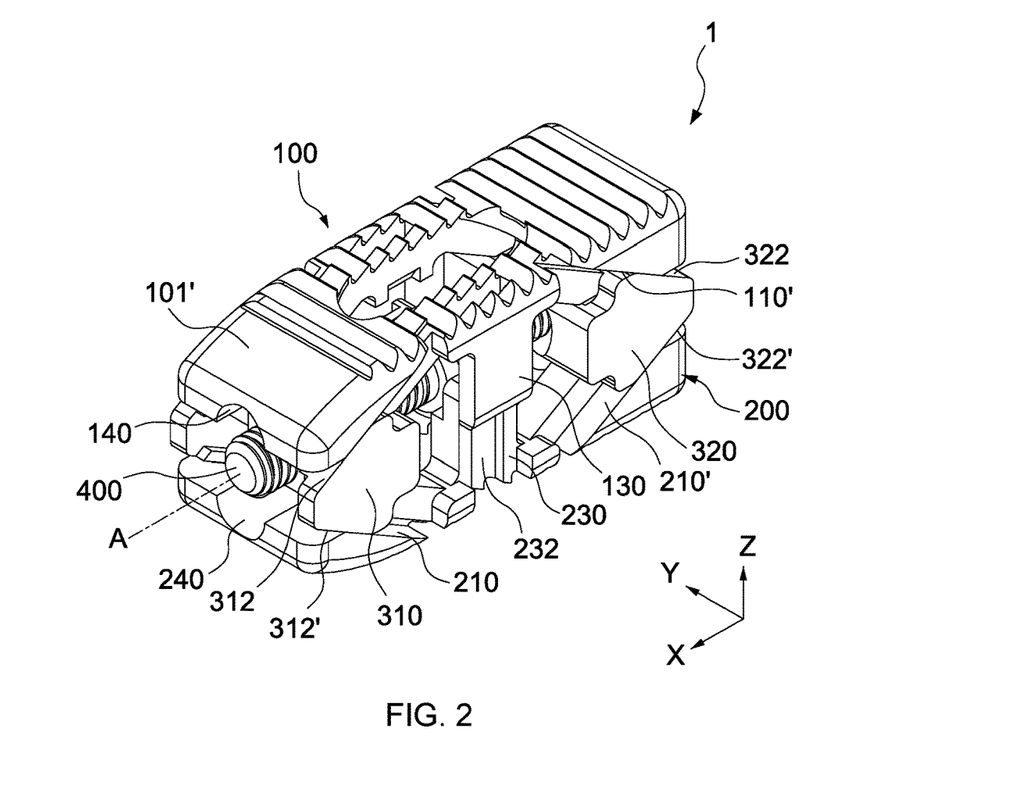
FIG. 2 illustrates the perspective view of the spinal interbody cage in an expandable state of one embodiment of the subject invention.

Firstly, refer to FIG. 1 and FIG. 2, which disclose the perspective view of the spinal interbody cage 1 under the state of the minimum height and being expanded in one embodiment of the subject invention. In order to clearly describe the embodiment of the subject invention, the direction of the long axis X, lateral direction Y and vertical direction Z are defined.

As shown in the figures, the spinal interbody cage 1 comprises a first end 11, a second end 12, a first side 13 and a second side 14, wherein the first end 11 and the second end 12 are opposite each other in the direction of the long axis X of the spinal interbody cage 1, the first side 13 and the second side 14 are opposite each other in the lateral direction Y of the spinal interbody cage 1, and the spinal interbody 1 has a central area between the first end 11 and the second end 12 and a height in the vertical direction Z.

As shown in FIG. 1, the spinal interbody cage 1 has an upper plate 100, a lower plate 200, a first slide block 310, a second slide block 320 and a screw arbor 400, wherein the first slide block 310, the second slide block 320 and the screw arbor 400 are disposed between the upper plate 100 and the lower plate 200. By rotating the screw arbor 400 clockwise in the direction of the long axis, the first slide block 310 and the second slide block 320 distance themselves from each other along the direction of the long axis X, and the upper plate 100 is driven to distance itself from the lower plate 200 along the vertical direction Z; by means of the above approach, the spinal interbody cage 1 of FIG. 1 can be adjusted to the expanded state as shown in FIG. 2.

On the other hand, the screw arbor 400 can also be rotated counterclockwise in the direction of the long axis so that the upper plate 100 will approach the lower plate 200 in the vertical direction Z and the height of the spinal interbody cage will decrease. The variation of the distance between the upper plate 100 and the lower plate 200 of the spinal interbody cage in the Z direction relates to the setting of the height of the interbody cage to be implanted into the human spine. The design in terms of the relation between the clockwise or counterclockwise rotation of the screw arbor 400 and the upper plate 100 or lower plate 200 moving upward or downward away or approaching each other can be altered as needed.

It is worth mentioning that the spinal interbody cage 1 of the subject invention permits the upper plate 100 to be adjusted to distance itself from or approach the lower plate 200, so it is easier to set the height of the spinal interbody cage 1 during surgery compared with the incremental adjustment approach. The continuous adjustment approach mentioned in the subject application implies that the spinal interbody cage 1 can be fixed at any height within a certain range. With the incremental adjustment approach, in contrast, the spinal interbody cage 1 is subject to the design of the structure and thus can only be fixed at several heights that are set beforehand.

Figure 3:
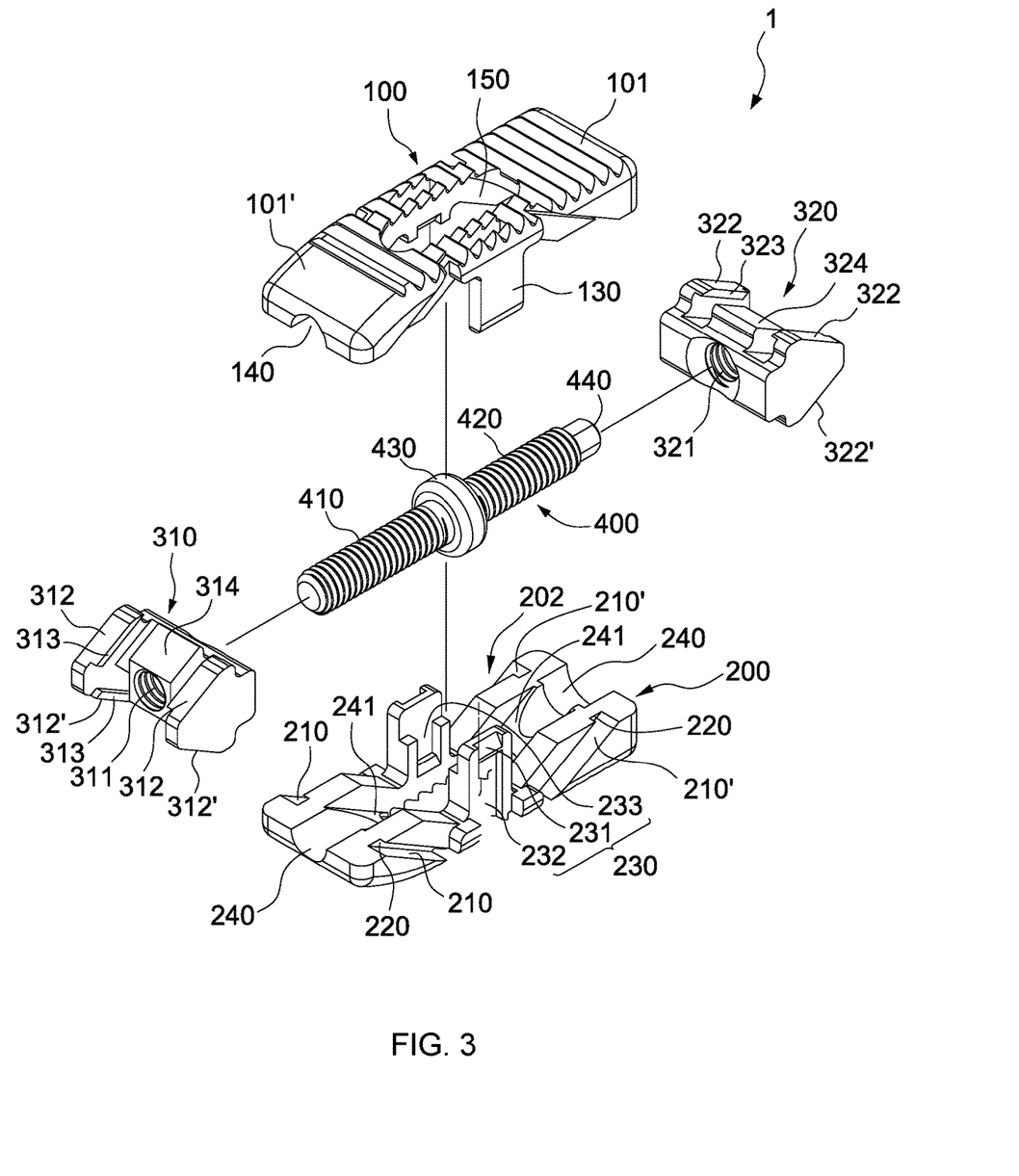
FIG. 3 illustrates the explosive view of the spinal interbody cage of one embodiment of the subject invention from above.
Figure 4:
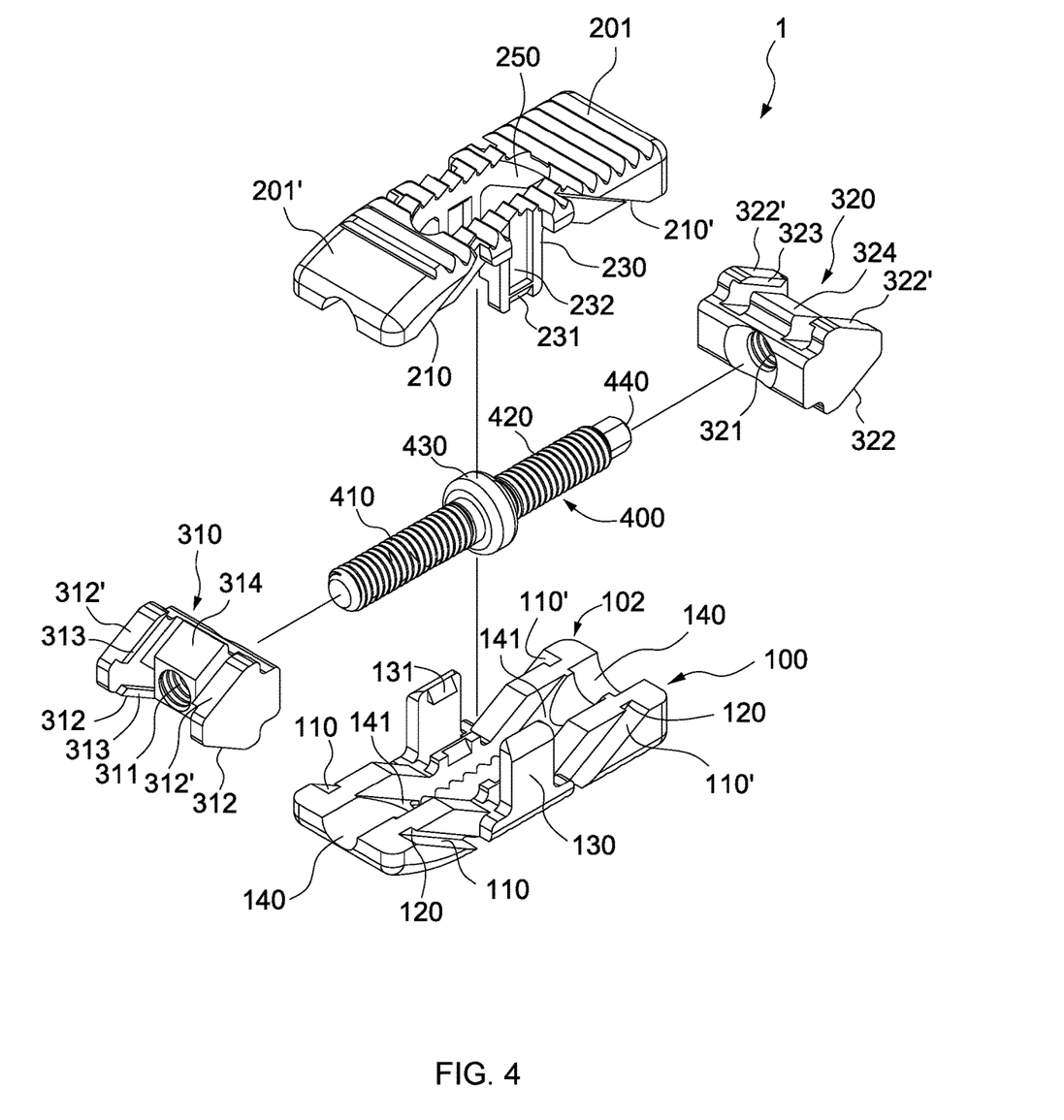
FIG. 4 illustrates the explosive view of the spinal interbody cage of one embodiment of the subject invention from above.
Figure 5A:
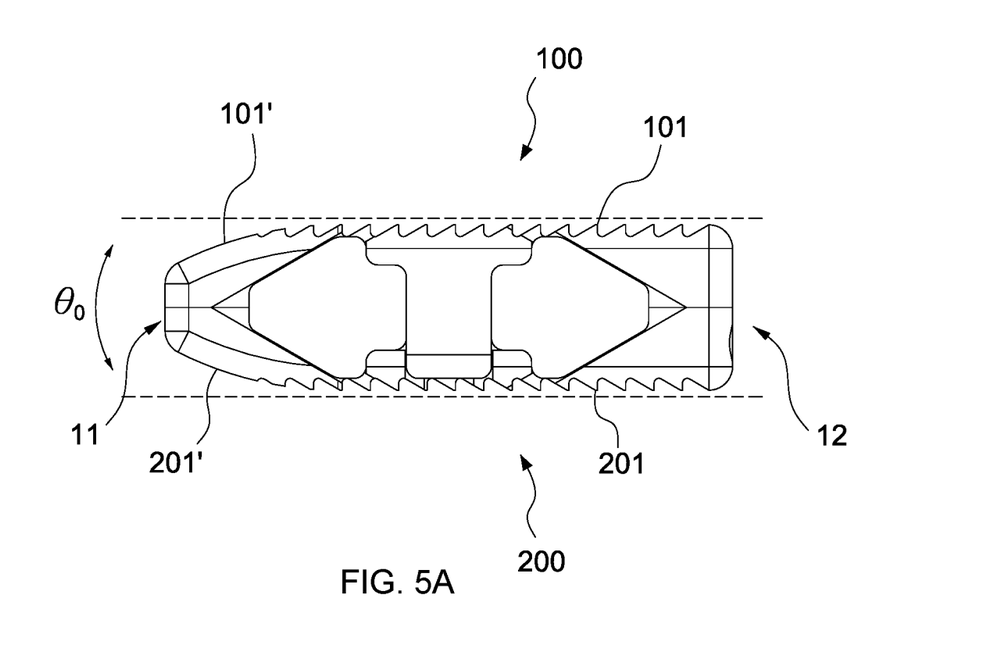
FIGS. 5A to 5D illustrate side views of different embodiments of the subject invention.
Figure 5B:
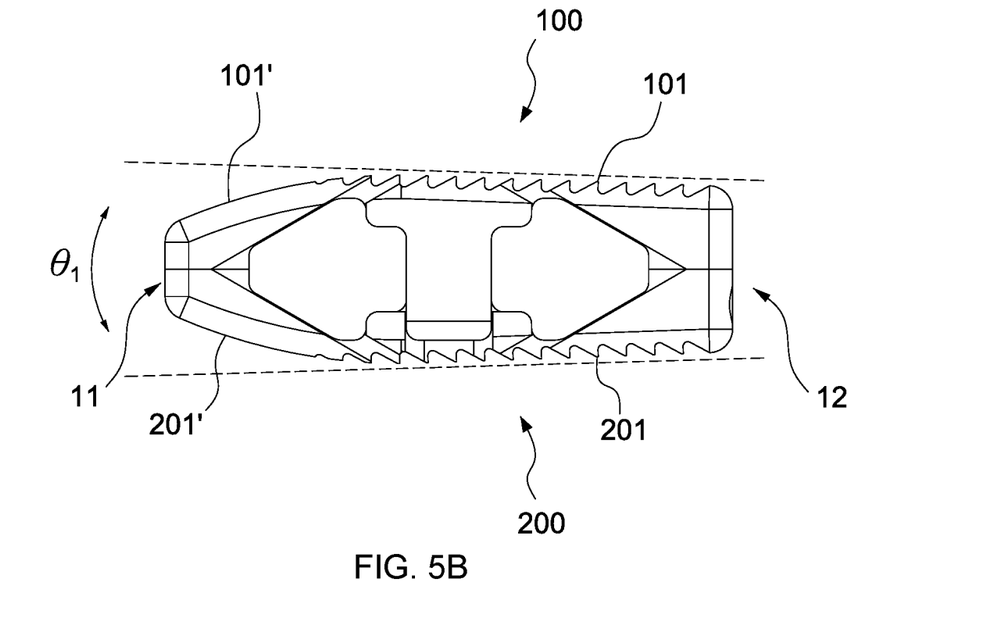
Figure 5C:
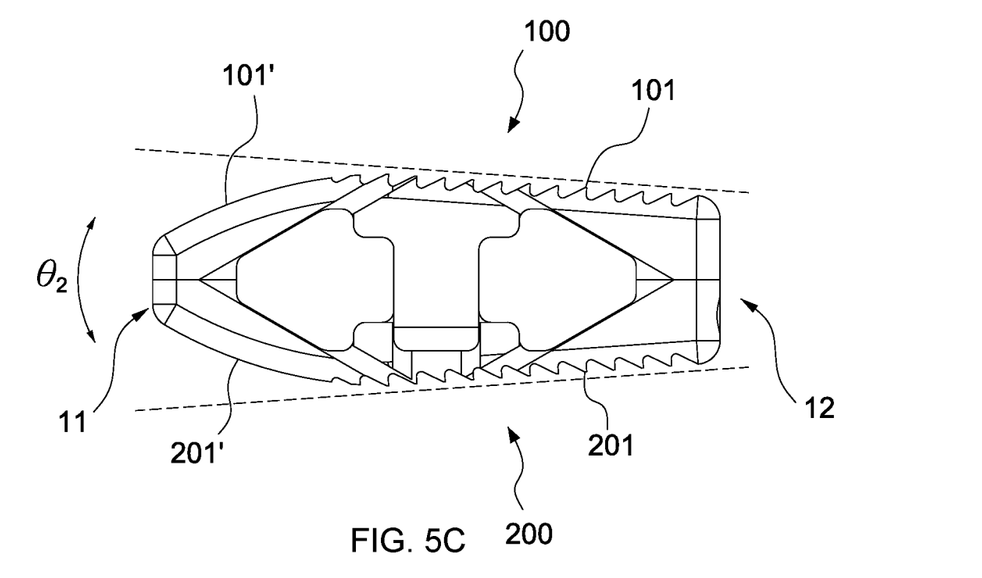
Figure 5D:
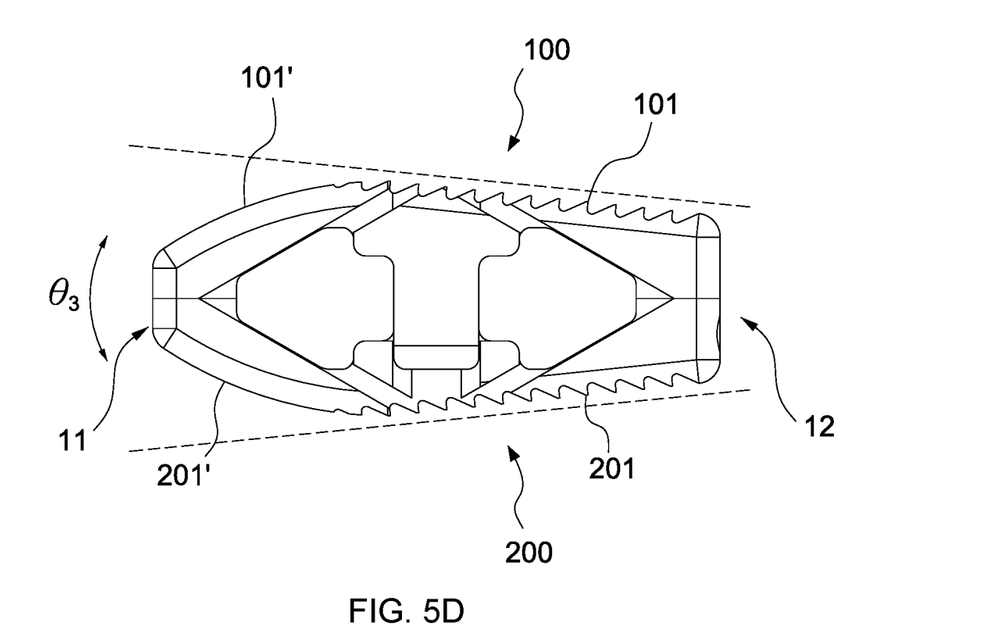

With reference to FIG. 3 and FIG. 4, the following description details structure of the spinal interbody cage 1 of one embodiment of the subject invention. FIG. 3 illustrates the explosive view of the spinal interbody cage 1 of FIG. 1 from above. FIG. 4 illustrates the explosive view of the spinal interbody cage 1 of FIG. 1 from below.

In order to make it easier to put the spinal interbody cage 1 between the human vertebrae, it is better to have shorter distance between the outer surfaces of the upper plate 100 and the lower plate 200 at the location close to the first end 11 and gradually larger distance toward the central area. As shown in FIG. 3 and FIG. 4, the upper plate 100 has a first upper plate surface 101 and a second upper plate surface 102, wherein the first upper plate surface 101 is distant from the lower plate 200 with respect to the second upper plate surface 102. On the other hand, the lower plate 200 has a second lower plate surface 202 facing the upper plate 100 and a first lower plate surface 201 with its back facing the upper plate 100. The upper plate 100 and the lower plate 200 further have a curved surface 101' and 201' respectively, the curved surfaces 101' and 201' adjacent to the central area gradually approach the second upper plate surface 102 and the second lower plate surface 202 respectively in a direction extending from the first upper plate surface 101 and the second upper plate surface 102 respectively to the first end 11, such that the distance between the curved surfaces 101' and 201' at the first end 11 is smaller than that adjacent to the central area. It is also allowable to dispose only one of the curved surfaces 101' or 201'. By means of the disposition of the curved surfaces, the spinal interbody cage will have a smaller area (thickness) at the first end relative to the cross-section in the direction of the Z axis of the second end or of the central area. Therefore, it is possible, during the implant surgery, to insert the first end 11 into a human body or between human vertebrae and to make the whole implantation process of the spinal interbody cage easier with the guidance of those curved surfaces. It should be noted that it is also acceptable to dispose a curved surface on the upper plate 100 or the lower plate 200 so as to provide the first end with a smaller front end surface (first cross-section area) and the second end with a larger area.

In addition, the first upper plate surface 101 and the first lower plate surface 201 may have a plurality of grooves so that they are serrate and the frictional force between the spinal interbody cage 1 and the vertebrae will increase, which will prevent the implanted spinal interbody cage 1 from sliding between the vertebrae. Each of the upper plate 100 and the lower plate 200 has at least one through hole (150 and 250, respectively) so that the self-bone or artificial bone tissue may be filled therein to achieve a better bone fusion rate. In the spirit of the subject invention, the through holes 150 and 250 can also be replaced with a concave shape depending on the demand.

As shown in FIG. 3 and FIG. 4, the screw arbor 400 comprises a first section 410, a second section 420 and a partition member 430, wherein the partition member 430 provides two functions: the first is to separate the first section 410 and the second section 420 of the screw arbor so that while the first slide block 310 and the second slide block 320 are moving toward each other along the direction of the long axis X on the screw arbor 400, they can at most only reach the terminal point of the central portion of their individual sections; the other function provides orientations of the first slide block 310 and the second slide block 320 with respect to the upper plate 100 and the lower plate 200 on the screw arbor 400; such function is achieved by an annular lateral protruding portion formed by the partition member 430 in the middle of the screw arbor 400, wherein the lateral protruding portion is constrained in the guide recess 233 formed by either the upper plate or the lower plate. And the first section 410 and the second section 420 have outer threads in opposite directions. In addition, the screw arbor 400 further comprises an operational end having a structure, for example, outer hexagonal structure, square structure or structure in plum blossom shape so that the screw arbor 400 can be rotated with a tool having the mating structure, e.g., outer hexagonal structure.

The upper plate 100 has a pair of first upper plate slanted surfaces 110 and a pair of second upper plate slanted surfaces 110' on the first section 410 and the second section 420 adjacent to the screw arbor 400 respectively; the upper plate slanted surfaces 110 and 110' extend from the second upper plate surface 102 toward the first upper plate surface 101 in the direction toward the central area on the first end 11 and the second end 12 respectively. The lower plate 200 has a pair of first lower plate slanted surfaces 210 and a pair of second lower plate slanted surfaces 210' on the first section 410 and the second section 420 adjacent to the screw arbor 400 respectively; the lower plate slanted surfaces 210 and 210' extend from the second lower plate surface 202 toward the first upper plate surface 201 in the direction toward the central area on the first end 11 and the second end 12 respectively. In one of the embodiments of the subject invention as shown in FIG. 3 and FIG. 4, one of the upper plate slanted surfaces of the first upper plate slanted surfaces 110 and one of the upper plate slanted surfaces of the second upper plated slanted surfaces 110' are located on the first side 13, and the other one of the upper plate slanted surfaces of the first upper plate slanted surfaces 110 and the other one of the upper plate slanted surfaces of the pair of second upper plated slanted surfaces 110' are located on the second side 14; one of the lower plate slanted surfaces of the first lower plate slanted surfaces 210 and one of the lower plate slanted surfaces of the second lower plated slanted surfaces 210' are located on the first side 13, and the other one of the lower plate slanted surfaces of the pair of second lower plate slanted surfaces 210 and the other one of the lower plate slanted surfaces of the pair of second upper plated slanted surfaces 210' are located on the second side 14. The effects of the first and second upper plate slanted surfaces 110, 110' and the first and second lower plate slanted surfaces 210, 210' are further described in the following content.

Moreover, the upper plate 100 further comprises an upper plate protruding portion 130 on the first side 13 and the second side 14 respectively, wherein the upper plate protruding portion 130 protrudes toward the lower plate 200 and has an upper plate constraint member 131, and the lower plate 200 further comprises a lower plate protruding portion 230 on the first side 13 and the second side 14 respectively, wherein the lower plate protruding portion 230 protrudes toward the upper plate 100 and has a lower plate constraint member 231 and a recess 232. The upper plate constraint member 131 and the lower plate constraint member 231 are configured and cooperate with each other to define a maximum distance between the first upper plate surface 101 and the first lower plate surface 210, i.e., the maximum value of the height of the spinal interbody cage 1, so as to prevent the upper plate 100 from completely separating from the lower plate 200 during the process of expansion. In this embodiment, the upper plate constraint member 131 forms a lateral bulge from the upper plate protruding portion 130 disposed in the recess 232 of the lower plate protruding portion 230, and the maximum height of the spinal interbody cage 1 is defined by the lower plate constraint member 231 of the lower plate protruding portion 230 abutting against the upper plate constraint member 131.

It is worth mentioning that the upper plate constraint member 131 and the lower plate constraint member 231 have a slanted surface on one side facing the lower plate and the upper plate respectively so that the upper plate constraint member 131 can go through the lower plate constraint member 231 and be disposed in the recess 232 of the lower plate protruding portion 230 by means of the installation and guidance of the slanted surface. It should be noted that the designs of the upper plate protruding portion and the lower plate protruding portion of the subject invention are not limited to the above embodiments; other equivalent modifications or replacement are also included in the spirit of the subject invention; for example, the maximum height of the spinal interbody cage 1 can be defined by the individual bulge or bulges in other forms and/or recesses of the upper plate protruding portion and the lower plate protruding portion.

With reference to FIG. 1 and FIG. 2 again, by means of the upper plate protruding portion 130 and/or the lower plate protruding portion 230, when the screw arbor is rotating in one direction and the upper plate 100 is approaching the lower plate 200 to the extent that the spinal interbody cage is of the minimum height (FIG. 1), the upper plate protruding portion 130 and/or the lower plate protruding portion 230 abut against one side of the slide blocks 310 and 320 in the direction of the long axis X to constrain the slide blocks 310 and 320 from further approaching each other.

The first slide block 310 and the second slide block 320 have a through hole 311 and 321 with inner thread respectively, the outer thread of the first section 410 of the screw arbor 400 is disposed in and cooperates with the inner thread of the first slide block 310, and the outer thread of the second section 420 of the screw arbor 400 is disposed in and cooperates with the inner thread of the second slide block 320, such that the slide blocks are disposed between the upper plate 100 and the lower plate 200.

In addition, the first slide block 310 has two pairs of slide block slanted surfaces 312 and 312' that are laterally opposite respectively, and the second slide block 320 also has two pairs of slide block slanted surfaces 322 and 322' that are laterally opposite respectively. Referring to FIG. 2 and FIG. 3, the structure of the first slide block 310 and the second slide block 320 can be substantially identical; the slide block slanted surfaces 312 and 312' of the first slide block 310 are adjacent to and abut against the first upper plate slanted surface 110 and the first lower plate slanted surface 210 respectively; and the slanted surfaces 322 and 322' of the second slide block 320 are adjacent to and abut against the second upper plate slanted surface 110' and the second lower plate slanted surface 210' respectively.

With the aforementioned arrangement, when the screw arbor 400 is rotating, since the outer threads of the first section 410 and the second section 420 are of opposite direction, the first slide block 310 and the second slide block 320 distance themselves from or approach each other in the direction of the long axis; with the arrangement of the slide block slanted surfaces, the upper plate slanted surface and the lower plate slanted surface, the slide blocks distancing from each other causes the first upper plate surface 101 to distance itself from the first lower plate surface 102 (namely, the height of the spinal interbody cage 1 gradually increases), and the slide blocks moving closer to each other causes the first upper plate surface 101 to approach the first lower plate surface 102 (namely, the height of the spinal interbody cage 1 gradually decreases). In other words, by rotating the screw arbor 400 clockwise or counterclockwise, the height of the spinal interbody cage can be increased or decreased continuously.

It is worth mentioning that the pair of first upper plate slanted surfaces 110 are parallel to the pair of second lower plate slanted surfaces 210', the pair of second upper plate slanted surfaces 110' are parallel to the pair of first lower plate slanted surface 210. Further, with respect to the surface (Y-Z surface) perpendicular to the line of the axis A of the screw arbor 400, the pair of first upper plate slanted surfaces 110 and the second upper plate slanted surfaces 110' are symmetric, and the pair of first lower plate slanted surfaces 210 and the pair of second lower plate slanted surfaces 210' are also symmetric. Therefore, when the first slide block 310 and the second slide block 320 are moving on the screw arbor 400, the slide block slanted surfaces constantly abut against one of the upper plate slanted surfaces 110, 110' or the lower plate slanted surfaces 210, 210' respectively so as to change the height of the spinal interbody cage 1 continuously, smoothly, and steadily, and provide the whole structure of the spinal interbody cage with more stable support.

In addition, in one of the embodiments of the subject invention, the length of the screw arbor 400 is equal to or smaller than the longitudinal length of the upper plate 100 and the lower plate 200, and the screw arbor 400 is disposed between the upper plate 100 and the lower plate 200 so that the screw arbor 400 will be maintained between the two ends of the upper plate 100 and the lower plate 200 (namely, the screw arbor 400 does not exceed the upper plate 100 or the lower plate 200 in the direction of the longitudinal length) during the aforementioned process of adjusting the spinal interbody cage 1. In another embodiment of the subject invention, the spinal interbody cage 1 can be configured, for example, to adjust the slide block slanted surfaces 312, 312', 322, 322', upper and lower plate slanted surfaces 110, 110', 210, 210', or the upper plate constraint member 131 and the lower plate constraint member 231 so that when the screw arbor 400 is rotated to cause the slide blocks distance themselves from each other and achieve the maximum height defined by the upper plate and the lower plate, the slide blocks do not exceed the two ends of the upper plate and the lower plate. Therefore, the longitudinal length of the spinal interbody cage 1 does not change during the process of adjusting the height, which is advantageous to prevent the compression of the nerves and tissues adjacent to the vertebrae as a result of the structure protruding the upper plate and the lower plate in the direction of the longitudinal length X.

Furthermore, the second upper plate surface 102 has an upper plate curved groove 140 on the first end 11 and the second end 12 respectively and the second lower plate surface 202 has a lower plate curved groove 240 on the first end 11 and the second end 12 respectively. When the spinal interbody cage 1 is adjusted to be smaller than a certain height, the upper plate curved grooves 140 and the lower plate curved grooves 240 are just able to accommodate the screw arbor 400. As shown in FIG. 1, when the upper plate 100 is closest to the lower plate 200 and the values of the height of the spinal interbody cage 1 is of the minimum value, the upper plate curved grooves 140 and the lower plate curved grooves 240 cooperate with each other on the first end 11 and the second end 12 so as to form a circular aperture on the first end 11 and the second end 12 which can completely accommodate and surround the screw arbor 400.

In addition, the upper plate 100 and the lower plate 200 comprise middle slanted surfaces 141 and 241 adjacent to the upper plate curved grooves 140 and the lower plate curved grooves 240 on the first end 11 and the second end 12 respectively, the middle slanted surfaces 141 and 241 extend from the second upper plate surface 102 to the first upper plate surface 101 and from the second lower plate surface 202 to the first lower plate surface 201 on the first end 11 and the second end 12 respectively, and the middle slanted surfaces 141 and 241 are parallel to the adjacent first upper plate slanted surfaces 110, the second upper plate slanted surfaces 110', the first lower plate slanted surface 210 or the second lower plate slanted surfaces 210'. On the other hand, the slide blocks 310 and 320 include middle slanted surfaces 314 and 324 on the location adjacent to the through hole 311, such that when the slide blocks 310 and 320 are moving with respect to the upper plate 100 and the lower plate 200, the middle slanted surfaces 314 and 324 of the slide blocks abut against and cooperate with the middle slanted surfaces 141 and 241 of the upper plate 100 and the lower plate 200, so as to cause the upper plate 100 to move further from or closer to the lower plate 200 by means of letting the slide blocks 310 and 320 be distant from or close to each other and provide the spinal interbody cage 1 with more stable supportive forces in the vertical direction Z and the direction of the long axis X.

Referring to FIG. 3 and FIG. 4 again, the upper plate 100 may further comprise upper plate guide members 120 correspondingly disposed adjacent to the upper plate slanted surfaces 110 and 110' respectively as lateral grooves, the lower plate 200 may comprise lower plate guide members 220 correspondingly disposed adjacent to the lower plate slanted surfaces 210 and 210' respectively as lateral grooves, and the upper plate guide members 120, wherein the lower plate guide members 220 are parallel to the corresponding upper plate slanted surfaces 110 and 110' or lower plate slanted surfaces 210 and 210' respectively. The slide blocks may further include slide block guide members 313 and 323 respectively that are correspondingly disposed adjacent to the slide block slanted surfaces 312, 312', 322 and 322' as lateral protruding rails, and the slide block guide members 313 and 323 are parallel to the corresponding slide block slanted surfaces 312, 312', 322 and 322' respectively, wherein the protruding rails of the slide block guide members 313 and 323 are disposed in the grooves of the upper plate guide members 120 and the lower plate guide members 220 respectively. By such means, when the screw arbor 400 is rotating and causes the slide blocks 310 and 320 to move away from or closer to each other, the protruding rails of the slide block guide members 313 and 323 are guided by the grooves and move along the direction of the grooves; therefore, in the direction other than the lateral direction Y, the directions of axes of the upper plate slanted surface and the lower plate slanted surface, the movements of the slide blocks with respect to the upper plate or the lower plate are constrained by the upper plate and lower plate guide members. It should be noted that although the drawings of the subject invention illustrate four upper plate guide members 120 and four lower plate guide members 220 corresponding to the upper plate slanted surfaces 110 and the lower plate slanted surfaces 210 respectively, the spinal interbody cage of the subject invention is not limited to a particular number of the upper plate guide members or lower plate guide members; for example, it is also possible that a single upper plate guide member and a single lower plate guide member cooperate with the guide members of the first slide block and the second slide block respectively.

In addition, the lower plate 200 has a guide recess 233 on the central area of the second lower plate surface 202, where the guide recess 233 is a lateral recess perpendicular to the second lower plate surface 202 and serves to accommodate the partition member 430, such that during rotation of the screw arbor 400 to separate the upper plate 100 and the lower plate 200 and increase the height of the spinal interbody cage 1, the partition member 430 of the screw arbor 400 is constrained to move in the guide recess, and the screw arbor 400 is thus constrained to move with respect to the upper plate 100 and the lower plate 200 in the vertical direction Z.

By means of the above arrangements, the spinal interbody cage 1 of the subject invention will have the effect of continuous, smooth, and stable adjustment of the spinal interbody cage and provide the structure of the spinal interbody cage with more stable support as a result of the arrangements of the slide block slanted surfaces, the upper plate slanted surfaces and the lower plate slanted surfaces. Moreover, when the height of the spinal interbody cage 1 of the subject invention is adjusted, the screw arbor 400 and the slide blocks 310 and 320 do not exceed the two ends of the upper plate 100 and the lower plate 200, such that the volume of the spinal interbody cage can be reduced and the compression of the nerves and tissues adjacent to the vertebrae can be prevented.

Moreover, referring to FIGS. 5A-5D, the first upper plate surface and the second upper plate surface may be disposed so that they have an angle $\theta$ (e.g., 0 to 15 degrees) along the direction of the screw arbor X, which provides support at a certain angle of the vertebrae that meets the requirements of the surgery. FIGS. 5A-5D describe the spinal interbody cage of the embodiment, wherein the same elements are designated with the reference numerals of the foregoing embodiments. Take the example of the condition that the upper plate 100 is approaching the lower plate 200 to the extent that the spinal interbody cage is of a minimum height. At that time, the upper plate 100 and the lower plate 200 abut against the first slide block 310 and the second slide block 320 respectively. The shapes or angles of the first upper plate surface 101 and the second upper plate surface 201 can be altered directly by changing the thickness of the upper plate 100 and the lower plate 200 close to the first end 11 and the second end 12. Or under the condition when the upper plate 100 and the lower plate 200 do not attach to each other in the Z direction, so as to form an angle between the first plate surface 101 and the second plate surface 201, such angle can be $\theta 0$, $\theta 1$, $\theta 2$ or $\theta 3$, wherein $\theta 0$ is 0 degrees, $\theta 1$ is 4 degrees, $\theta 2$ is 8 degrees, $\theta 3$ is 12 degrees; or $\theta 3$ can also be 20 or 25 degrees. With the above arrangements, the angle of the supportive surface provided by the first plate surface 101 and the second plate surface can be determined by the spinal interbody cage of the subject invention, which further provides a supportive effect on the upper and lower vertebrae at a certain angle.

It should be understood that the subject invention is not limited to the certain structure or arrangement disclosed herein. Persons of ordinary skill in the art can understand that, in the spirit of the subject invention, the structures and arrangements disclosed may be altered or replaced. It should also be understood that the terminology and descriptions regarding the wording of the directions or relative positions are for the description of particular embodiments and for the convenience of explanation and understanding, and do not impose any limitation to the scope of the subject invention; the scope of the subject invention is only subject to the claims and their equivalents.

What is claimed is:

1. A spinal interbody cage comprising: p1 a first end and a second end opposingly arranged along a long axis X and a central area between the first end and the second end, a first side and a second side opposite each other in a lateral direction Y, and a height in a direction perpendicular to the direction of a longitudinal length and the lateral direction;
   an upper plate having a first upper plate surface and a second upper plate surface;
   a lower plate having a first lower plate surface facing away from the upper plate and a second lower plate surface facing the upper plate; wherein the first upper plate surface is more distant from the lower plate relative to the second upper plate surface;
   wherein the upper plate has upper plate protruding portions protruding toward the lower plate on the first side and the second side respectively, the upper plate protruding portions and the upper plate are formed integrally, the upper plate protruding portions have an upper plate constraint member respectively, and the lower plate has lower plate protruding portions protruding toward the upper plate on the first side and the second side respectively, the lower plate protruding portions and the lower plate are formed integrally, the lower plate protruding portions have a lower plate constraint member and a recess respectively, each upper plate constraint member is at least partly receivable in the recess of the corresponding lower plate protruding portion and slidable along the recess, wherein each upper plate constraint member is slidable along the recess to abut against the respective lower plate constraint member to define a maximum value of the height of the spinal interbody cage;
   a screw arbor disposed between the upper plate and the lower plate and having a first section and a second section, the sections having an outer thread respectively, wherein the outer thread of the first section and the outer thread of the second section are of opposite spiral direction; and
   a first slide block and a second slide block, wherein the first and second slide blocks are disposed between the upper plate and the lower plate and have a through hole having an inner thread, respectively, wherein the inner threads are of opposite spiral direction, wherein;

the upper plate has a pair of first upper plate slanted surfaces and a pair of second upper plate slanted surfaces respectively adjacent to the first section and the second section of the screw arbor, and the upper plate slanted surfaces extend, in a direction toward the central area, from the second upper plate surface to the first upper plate surface on the first end and the second end respectively;

the lower plate has a first lower plate slanted surface and a second lower plate slanted surface respectively adjacent to the first section and the second section of the screw arbor, wherein the first and second lower plate slanted surfaces extend, in the direction toward the central area, from the second lower plate surface to the first lower plate surface on the first end and the second end respectively;

the outer threads of the sections of the screw arbor are disposed in and cooperate with the inner threads of the first slide block and the second slide block; and the first slide block and the second slide block have two pairs of slide block slanted surfaces respectively, wherein the slide block slanted surfaces of the first slide block are adjacent to and abut against the pair of first upper plate slanted surfaces and the pair of first lower plate slanted surfaces and the slide block slanted surfaces of the second slide block are adjacent to and abut against the pair of second upper plate slanted surfaces and the pair of second lower plate slanted surfaces, such that when the screw arbor is rotating in a first direction, the first slide block distances from the second slide block and the height of the spinal interbody cage increases.

2. The spinal interbody cage of claim 1, wherein the pair of first upper plate slanted surfaces is parallel to the pair of second lower plate slanted surfaces, the pair of second upper plate slanted surfaces is parallel to the pair of first lower plate slanted surfaces, wherein the pair of first upper plate slanted surfaces and the pair of second upper plate slanted surfaces are symmetric with respect to a surface of an axis (A) perpendicular to the screw arbor, and the pair of first lower slanted surfaces and the pair of second lower plate slanted surfaces are symmetric with respect to a surface of the axis (A) perpendicular to the screw arbor.

3. The spinal interbody cage of claim 1, wherein the slide blocks, the upper plate and the lower plate are configured so that the slide blocks will not exceed the upper plate or the lower plate in the direction of the long axis when they are moving on the screw arbor.

4. The spinal interbody cage of claim 1, wherein the screw arbor includes an operational end with hexagonal structure so that the screw arbor can be rotated with such operational end.

5. The spinal interbody cage of claim 1, wherein:

the upper plate comprises at least an upper plate guide member which is correspondingly disposed adjacent and parallel to one of the upper plate slanted surfaces;

the lower plate comprises at least a lower plate guide member which is correspondingly disposed adjacent and parallel to one of the lower plate slanted surfaces; and the first slide block and the second slide block have at least a slide block guide member respectively, wherein the slide block guide members are correspondingly disposed adjacent to one of the slide block slanted surfaces respectively and cooperate with the upper plate guide member and the lower plate guide member so as to guide a relative movement of the slide blocks with the upper plate and the lower plate.

6. The spinal interbody cage of claim 5, wherein the slide block guide members are protruding rails and the upper plate guide member and the lower plate guide member are grooves, or the slide block guide members are grooves and the upper plate guide member and the lower plate guide member are protruding rails.

7. The spinal interbody cage of claim 1, wherein a length of the screw arbor is smaller or equal to lengths of the long axes of the upper plate and the lower plate.

8. The spinal interbody cage of claim 1, wherein the first upper plate surface has an upper plate curved groove on the first end and the second end respectively, and the second lower plate surface has a lower plate curved groove on the first end and the second end respectively, wherein when the screw arbor is rotating in a second direction opposite to the first direction and causes the first slide block to move toward the second slide block, and the height of the spinal interbody cage decreases, the upper plate curved grooves and the lower plate curved grooves serve to accommodate the screw arbor.

9. The spinal interbody cage of claim 8, wherein when the height of the spinal interbody cage has decreased to the a minimum, the upper plate curved grooves and the lower plate curved grooves form a circular aperture surrounding the screw arbor.

10. The spinal interbody cage of claim 1, wherein one or each of the upper plate and the lower plate has a curved surface, and the curved surfaces are configured to extend, near the central area, from the first upper plate surface or the first lower plate surface toward the first end so that thicknesses of the upper plate and the lower plate that are close to the first end decreases gradually.

11. The spinal interbody cage of claim 1, wherein one upper plate slanted surface of the pair of first upper plate slanted surfaces and one upper plate slanted surface of the pair of second upper plate slanted surfaces are located on the first side, and the other upper plate slanted surface of the pair of first upper plate slanted surfaces and the other upper plate slanted surface of the pair of second upper plate slanted surfaces are located on the second end; and one lower plate slanted surface of the pair of first lower plate slanted surfaces and one lower plate slanted surface of the pair of second lower plate slanted surfaces are located on the second side.

12. The spinal interbody cage of claim 1, wherein the first upper plate surface is set at an angle relative to the first lower plate surface to set an angle of vertebra surfaces desired to be supported by the first upper plate surface and the first lower plate surface.

13. The spinal interbody cage of claim 12, wherein the angle between the first plate surface and the first lower plate surface can be set as one of the following two: (1) 0-12 degrees, (2) 0-25 degrees.

14. A spinal interbody cage, comprising:

an upper plate having a plurality of upper plate slanted surfaces;

a lower plate having a plurality of lower plate slanted surfaces;

a screw arbor disposed between the upper plate and the lower plate and having a first section and a second section, the sections having an outer thread respectively, wherein the outer thread of the first section and outer thread of the second section are of opposite spiral direction; and a first slide block and a second slide block, wherein the slide blocks are disposed between the upper plate and the lower plate and have a through hole having an inner thread respectively, and the inner threads are of opposite spiral direction, wherein the outer threads of the screw arbor are disposed in and cooperate with the inner threads of the first slide block and the second slide block, and the screw arbor, the first slide block and the second slide block are disposed between the upper plate and the lower plate;

wherein the upper plate has a pair of upper plate protruding portions protruding toward the lower plate, the upper plate protruding portions and the upper plate are formed integrally, the member respectively, the lower plate has a pair of lower plate protruding portions protruding toward the upper plate, the lower plate protruding portions and the lower plate are formed integrally, the lower plate protruding portions are laterally opposite and have a lower plate constraint member and a recess respectively, each upper plate constraint member is at least partly receivable in the recess of the corresponding lower plate protruding portion and slidable along the recess, wherein each upper plate constraint member is slidable along the recess, wherein each upper plate constraint member is configured to define a maximum value of a height of the spinal interbody cage;

the upper plate slanted surfaces face the lower plate respectively, the lower plate slanted surfaces face the upper plate respectively, the first slide block and the second slide block include at least two slide block slanted surfaces respectively, and the slide block slanted surfaces abut against one of the upper plate slanted surfaces and the lower plate slanted surfaces respectively, wherein the upper plate slanted surfaces, the lower plate slanted surfaces and the slide block slanted surfaces are configured so that when the screw arbor is rotating in a first direction along a long axis X, the first slide block will be driven to distance itself from the second slide block and cause the upper plate to distance itself from the lower plate along vertical direction (Z).

15. The spinal interbody cage of claim 14, wherein the upper plate slanted surfaces are symmetric with respect to one surface perpendicular to an axis (A) of the screw arbor, and the lower plate slanted surfaces are symmetric with respect to one of the surfaces perpendicular to the axis (A) of the screw arbor.

16. The spinal interbody cage of claim 14, wherein when the height of the spinal interbody cage is at the maximum value, the slide blocks, the upper plate and the lower plate are configured to prevent the slide blocks, when moving on the screw arbor, from exceeding the upper plate or the lower plate in a longitudinal direction.

17. The spinal interbody cage of claim 14, wherein:

the upper plate includes an upper plate guide member correspondingly disposed adjacent and parallel to one of the upper plate slanted surfaces;

the lower plate includes an lower plate guide member correspondingly disposed adjacent and parallel to one of the lower plate slanted surfaces; and the slide blocks have at least one slide block guide member respectively, wherein the slide block guide members are correspondingly disposed adjacent to one of the slide block slanted surfaces and cooperate with the upper plate guide member and the lower plate guide member so as to guide the relative movement of the slide blocks between the upper plate and the lower plate.

18. The spinal interbody cage of claim 17, wherein the slide block guide members are protruding rails and the upper plate guide member and the lower plate guide member are grooves, or the slide block guide members are grooves and the upper plate guide member and the lower plate guide member are protruding rails.

19. The spinal interbody cage of claim 14, wherein length of the screw arbor is smaller than or equal to the longitudinal length of the upper plate and the lower plate.

20. The spinal interbody cage of claim 14, wherein the second upper plate surface has an upper plate curved groove on two ends of the upper plate respectively, and the second lower plate surface has a lower plate curved groove on two ends of the lower plate respectively, wherein when the screw arbor is rotating in a second direction opposite to the first direction along the long axis X, the first slide block approaches the second slide block such that when the upper plate approaches the lower plate and causes the height of the spinal interbody cage to decrease, the upper plate curved grooves and the lower plate curved grooves serve to accommodate the screw arbor.

21. The spinal interbody cage of claim 20, wherein when the height of the spinal interbody cage decreases to a minimum, the upper plate curved grooves and the lower plate curved grooves form a circular aperture which surrounds the screw arbor respectively.

22. The spinal interbody cage of claim 14, wherein the spinal interbody has a first cross-section area on a first end along the direction of the long axis (X), and has a second cross-section area on a second end along the direction of the long axis (X), wherein the first cross-section area is smaller than the second cross-section area.

23. The spinal interbody cage of claim 14, further comprising a first upper plate surface and a first lower plate surface, wherein the first upper plate surface is located on one end of the vertical direction (Z), the first lower plate surface is located on an other end of the vertical direction (Z), and the first upper plate surface and the first lower plate surface form an angle therebetween to set an angle of a vertebra surface to be supported between the first plate surface and the second plate surface.

* * * * *

UNITED STATES PATENT AND TRADEMARK OFFICE
CERTIFICATE OF CORRECTION

PATENT NO. : 10,682,239 B2
APPLICATION NO. : 15/864208
DATED : June 16, 2020
INVENTOR(S) : Shao-Keh Hsu, Chien-Yu Lin and Kuo-Wei Tseng It is certified that error appears in the above-identified patent and that said Letters Patent is hereby corrected as shown below:

In the Claims

| | | | |
|---|---|---|---|
| Claim 1, | Column 12, | Line 25, | change "comprising: p1 a first" to --comprising: a first-- |
| Claim 9, | Column 14, | Line 23, | change "decreased to the a" to --decreased to a-- |
| Claim 14, | Column 15, | Lines 22 & 23, | change "the recess, wherein each upper plate" to --the recess to abut against the respective lower plate-- |
| Claim 14, | Column 15, | Line 39, | change "plate along vertical" to --plate along a vertical-- |
| Claim 19, | Column 16, | Line 19, | change "14, wherein length" to --**14**, wherein a length-- |

Signed and Sealed this
Eleventh Day of August, 2020

Andrei Iancu
*Director of the United States Patent and Trademark Office*